United States Patent
Kee et al.

(10) Patent No.: US 12,186,162 B2
(45) Date of Patent: Jan. 7, 2025

(54) SYSTEM OF A PLURALITY OF CONTACTLESS ADHESIVE BANDAGES

(71) Applicants: Sarah Han Kee, Rockville, MD (US);
Emma Han Kee, Rockville, MD (US);
Nelson Moy Kee, Rockville, MD (US)

(72) Inventors: Sarah Han Kee, Rockville, MD (US);
Emma Han Kee, Rockville, MD (US);
Nelson Moy Kee, Rockville, MD (US)

( * ) Notice: Subject to any disclaimer, the term of this patent is extended or adjusted under 35 U.S.C. 154(b) by 136 days.

(21) Appl. No.: 17/501,169

(22) Filed: Oct. 14, 2021

(65) Prior Publication Data

US 2022/0117798 A1    Apr. 21, 2022

Related U.S. Application Data

(60) Provisional application No. 63/093,192, filed on Oct. 17, 2020.

(51) Int. Cl.
| | | |
|---|---|---|
| *A61F 13/02* | (2024.01) | |
| *A61F 13/0246* | (2024.01) | |
| *A61F 13/00* | (2006.01) | |

(52) U.S. Cl.
CPC ...... *A61F 13/0233* (2013.01); *A61F 13/0246* (2013.01); *A61F 13/0266* (2013.01); *A61F 2013/00165* (2013.01)

(58) Field of Classification Search
CPC ........ A61F 2013/00165; A61F 13/0233; A61F 13/0246; A61F 13/0266; A61F 13/00017; A61F 13/00025; A61F 13/00046; A61F 13/00089; A61F 13/00548; A61F 13/00936; A61F 13/025; A61F 13/00987; A61F 13/0206; A61F 13/0226; A61F 15/004; A61F 15/005; A61F 15/006;
(Continued)

(56) References Cited

U.S. PATENT DOCUMENTS 3,528,416 A * 9/1970 Chamberlain ........ A61F 15/008
128/888
3,908,645 A * 9/1975 Sandvig ............ A61F 13/0203
602/74

(Continued)

FOREIGN PATENT DOCUMENTS

WO    WO-2009049232 A1 * 4/2009 ....... A61F 13/00063
WO    WO-2016067015 A1 * 5/2016 ............. A61F 13/02

*Primary Examiner* — Ophelia A Hawthorne
*Assistant Examiner* — Michael Milo
(74) *Attorney, Agent, or Firm* — Nelson M. Kee

(57) ABSTRACT

A system of contactless adhesive bandages is taught that are customizable to extend and cover, but not touch, wounds that are long and/or curving. The system of contactless adhesive bandages comprises one or more sectional raised adhesive bandages sealed off at the ends of runs by end sectional raised adhesive bandages. The system of contactless adhesive bandages is preferably applied contiguously in an overlapping fashion to follow the contours of the wound. A raised adhesive bandage is taught that covers but does not contact the wound. The raised adhesive bandage comprises a strip having an upper surface and a lower surface. An adhesive is at least partially disposed on the lower surface. A pad is disposed on the adhesive and/or lower surface. Raised edges are disposed on the pad creating a hollowed-out area. Raised edges are dimensioned such that they and the pad are not in contact with the wound.

9 Claims, 6 Drawing Sheets

(58) Field of Classification Search
CPC .............. A61F 15/007; A61F 15/008; A61F 2013/00604; A61F 2013/00412; A61F 2013/00902; A61F 2013/00863; A61F 2013/00582; A61F 2013/00685; A61F 2013/00817; A61F 2013/00719; A61F 2013/00089; A61F 2013/00361; A61F 2013/0017; A61F 2013/00174; A61F 2013/00195; A61F 2013/002; A61F 2013/00182; A61F 2013/00919; A61F 2013/00914; A61F 2013/0091; A61F 2013/00846; A61F 7/007; A61F 2007/0088; A61F 2007/0078; A61F 2007/0071; A61M 25/02; A61M 2025/0206; A61M 2025/01213; A61M 2025/0246; A61M 2025/0253; A61M 2025/0266; A61B 46/23
USPC .... 602/54, 2, 14, 41, 43, 47, 52, 56, 57, 58; 604/180, 304, 308; 128/888, 889, 879, 128/892; 607/108, 114
See application file for complete search history.

(56) References Cited

U.S. PATENT DOCUMENTS

| | | | | |
|---|---|---|---|---|
| 2014/0330222 | A1* | 11/2014 | Bruder | A61F 13/124 604/290 |
| 2020/0000622 | A1* | 1/2020 | Lundh | A61F 13/06 |
| 2020/0383850 | A1* | 12/2020 | Storari | A61F 13/023 |

* cited by examiner

SYSTEM OF A PLURALITY OF CONTACTLESS ADHESIVE BANDAGES

FIELD

This invention relates to adhesive bandages, and more specifically, to adhesive bandages that cover but do not make contact with the wound.

BACKGROUND

When the skin, specifically the dermis (containing blood vessels, glands, and nerve endings), is cut, the body automatically responds by setting into a sequence of overlapping events called the "four phases of wound healing." The four phases of healing are Hemostasis, Inflammatory, Proliferative, and Maturation. During Hemostasis, the body's first objective is to stop blood from flowing out and bacteria and pathogens from entering in. To prevent both scenarios from occurring, the body forms a blood clot (scab) around the penetrated area. Inflammation is the second stage of wound healing and begins right after the injury when the injured blood vessels cause localized swelling. Inflammation both controls bleeding and prevents infection. Damaged cells, pathogens, and bacteria are removed from the wound area. The Proliferative stage focuses on filling and covering the damaged area. Fibroblast makes collagen to form connective skin tissue. The epidermal cells split to repair the outer layer of skin while the dermis contracts to close the penetrated area. During the Maturation process, spanning from a couple of weeks to years depending on the severity of the original injury, the new layer of skin slowly regains its former strength, yet it will only gain back about 80% of its original strength.

Adhesive bandages are commonly applied to cover and protect open wounds. There is much debate in the medical community about whether it is better to keep a wound (e.g., scrape, abrasion, cut) dry or wet and when to remove an adhesive bandage during the different phases to allow more exposure to oxygen to promote the most effective healing. Wet or moist treatment of wounds have been shown to promote re-epithelialization (during the final healing stage when the surface regenerates from the edges to cover the wound site) and results in reduced scar formation, as compared to treatment in a dry environment.

Although the understanding of wound healing has increased, adhesive bandage technology has not changed much since its inception. FIG. 1 shows a traditional prior art adhesive bandage 100 with an absorbent pad 104 disposed on an adhesive strip 103 that attaches to the user's skin. A traditional adhesive bandage 100 keeps the wound covered and dry as they are designed to press an absorbent pad 104 against the wound to keep it sterile using an adhesive strip. Traditional adhesive bandages 100 do a good job stopping and soaking up bleeding. A wound typically "seals up" about 24 hours after applying a traditional adhesive bandage 100. Because oxygen is essential to the wound healing process, most doctors encourage patients to remove traditional adhesive bandages 100 after a day. If a traditional adhesive bandage 100 is kept on much longer, healing is impeded because the wound is too dry and lacks exposure to oxygen. At some point during the healing process, most people will take the traditional adhesive bandage 100 off to allow the wound to more efficiently and fully heal. This, however, exposes the not fully healed wound to dirt or debris, that could lead to infection. Moreover, scabs that do develop without a covering are exposed to the surroundings and are susceptible to being torn off thereby restarting and delaying the healing process.

Therefore, there is a need for an improved adhesive bandage that can cover but not touch the wound. This contactless adhesive bandage can be used after the initial stage(s) of healing to keep the wound sterile and to allow exposure to oxygen for faster and safer healing than traditional adhesive bandages that press against the wound.

Traditional adhesive bandages also do a poor job with long and/or curving wounds. Their fixed sizes do not provide the flexibility necessary to cover such odd shaped wounds without the pad and/or adhesive touching the wound. This problem of contacting the wound also exists when applying multiple traditional adhesive bandages. Therefore, there is a need for an improved system of contactless adhesive bandages that are customizable to extend and cover, but not touch, wounds that are long and/or curving.

BRIEF SUMMARY OF THE INVENTION

In one embodiment, a raised adhesive bandage is provided that covers but does not contact the wound. The raised adhesive bandage comprises a strip having an upper surface and a lower surface. An adhesive is at least partially disposed on the lower surface. A pad is disposed on the adhesive and/or lower surface. Raised edges are disposed on the pad creating a hollowed-out area. Raised edges are dimensioned such that they and the pad are not in contact with the wound. At least one protective release tab is removably disposed on the adhesive and/or lower surface.

In one embodiment, a system of plurality of contactless adhesive bandages is customizable to extend and cover, but not touch, wounds that are long and/or curving. The system of contactless adhesive bandages comprises one or more sectional raised adhesive bandages sealed off at the ends of runs by end sectional raised adhesive bandages. The system of contactless adhesive bandages is preferably applied contiguously in an overlapping fashion to follow the contours of the wound.

In one embodiment, a sectional raised adhesive bandage is provided that can be applied over (but not touching) long and/or curved wounds that cannot be effectively covered by a single raised adhesive bandage. The sectional raised adhesive bandage comprises a sectional strip having a sectional upper surface and a sectional lower surface. An adhesive is at least partially disposed on the sectional lower surface. A sectional pad is disposed on the adhesive and/or sectional lower surface. At least two sectional raised edges are disposed on the sectional pad creating a channeled-out area. Sectional raised edges are dimensioned such that they and the sectional pad are not in contact with the wound. At least one protective release tab is removably disposed on the adhesive and/or sectional lower surface.

In one embodiment, an end sectional raised adhesive bandage is provided that can be applied at the ends to close off one or more sectional raised adhesive bandages. The end sectional raised adhesive bandage comprises an end sectional strip having an end sectional upper surface and an end sectional lower surface. An adhesive is at least partially disposed on the end sectional lower surface. An end sectional pad is disposed on the adhesive and/or sectional lower surface. An end sectional raised adhesive bandage is created by disposing end sectional raised edges on one to three sides of the end sectional pad.

DETAILED DESCRIPTION OF THE INVENTION

Figure 1:
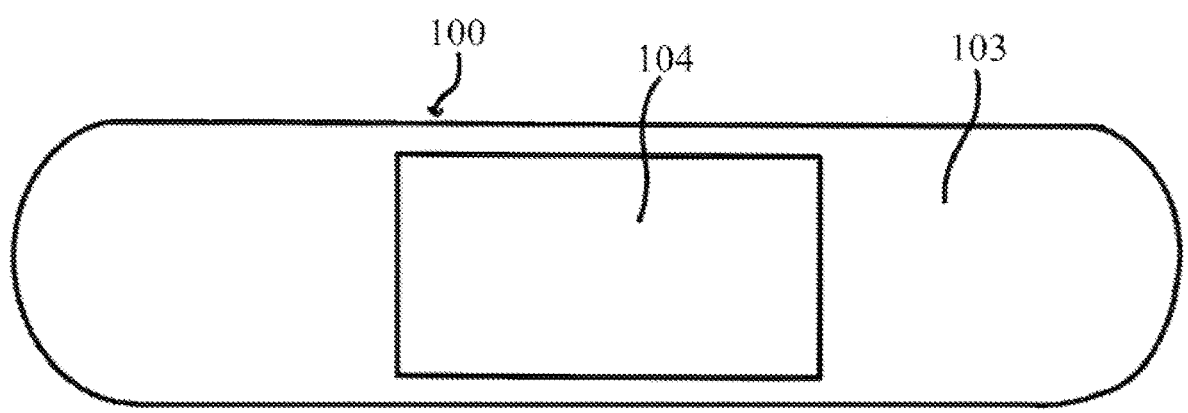
FIG. 1 is a bottom plan view (facing the skin and wound) of a traditional prior art adhesive bandage that contacts the wound.
Figure 2A:
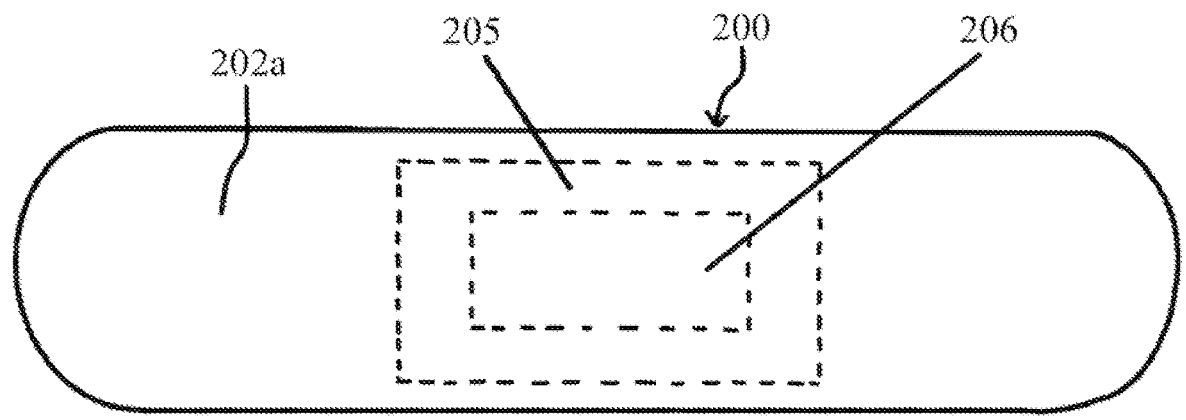
FIG. 2A is a top plan view (facing away from the skin and wound) of a preferred embodiment of the raised adhesive bandage of the present invention where the raised edges separate the pad from the wound.
Figure 2B:
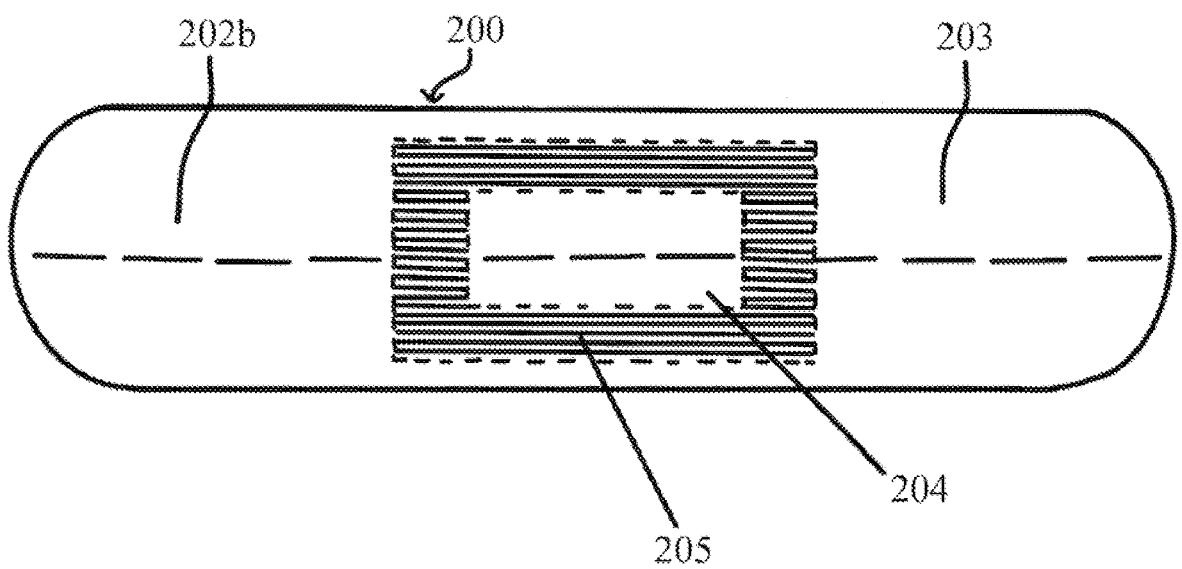
FIG. 2B is a bottom plan view (facing the skin and wound) of a preferred embodiment of the raised adhesive bandage of the present invention where the raised edges are positioned such that the hollowed-out area separates the pad from the wound.
Figure 2C:
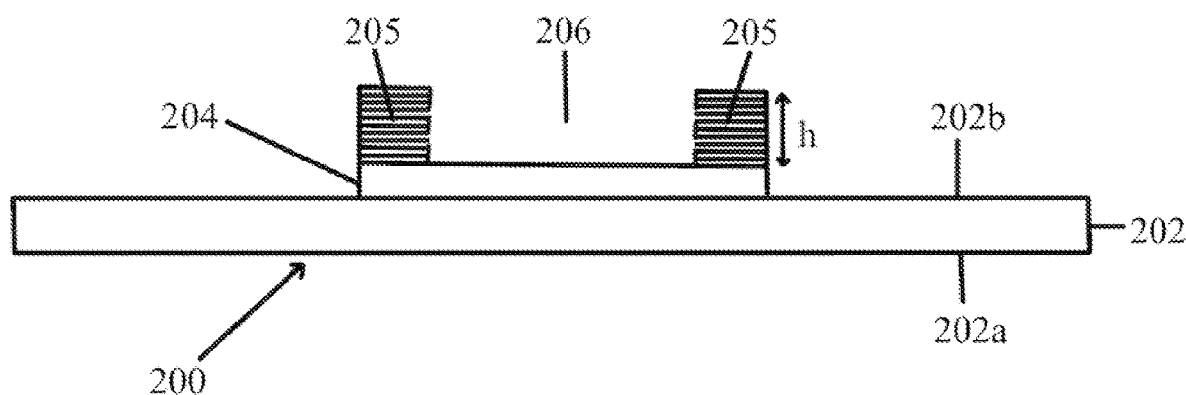
FIG. 2C is a side cut-away slice of a preferred embodiment of the raised adhesive bandage of the present invention viewed along the center dashed line of FIG. 2B.
Figure 2D:
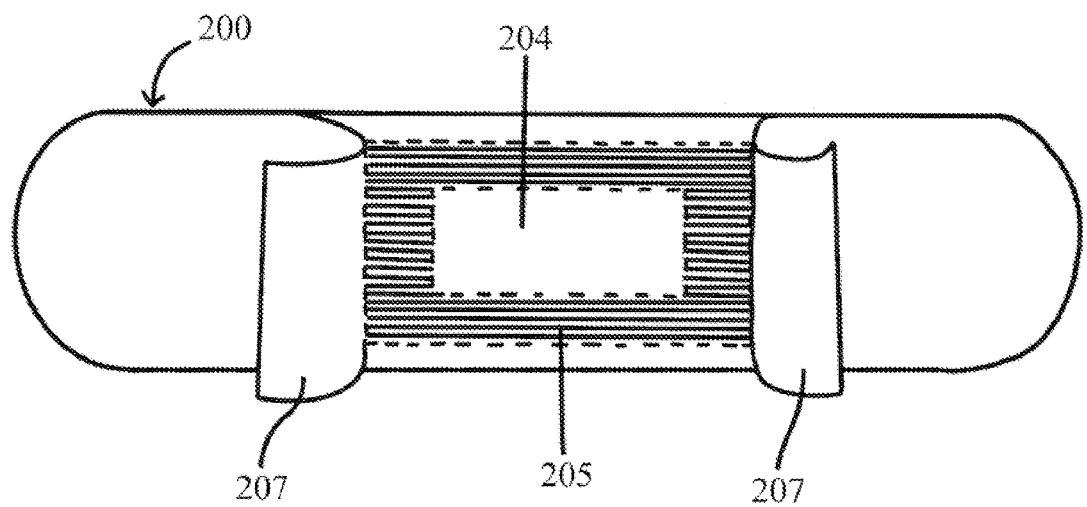
FIG. 2D is a bottom plan view (facing the skin and wound) of a preferred embodiment of the raised adhesive bandage of the present invention with a pair of protective release tabs.

The present invention is directed to adhesive bandages that are manufactured, made, and/or provided to preferably not contact the wound.

I. Raised Adhesive Bandage

FIGS. 2A-2D show an embodiment of a raised adhesive bandage 200 of the present invention. Raised adhesive bandage 200 preferably includes a strip 202 having an upper surface 202a that faces away from the skin and a lower surface 202b that faces the skin, an adhesive 203, a pad 204, raised edges 205 that create a hollowed-out area 206, and a pair of protective release tabs 207 (identified singularly and plurally as "207"). Adhesive 203 is at least partially disposed on lower surface 202b and contacts a user's skin, Pad 204 is disposed on lower surface 202b and/or adhesive 203. Raised edges 205 are disposed on the pad 204 and/or adhesive 203 creating a hollowed-out area 206. Raised edges 205 can be one continuous shape or comprised of multiple separate shapes. Raised edges 205 can, but do not have to, extend to the outer edges of the pad 204. A single or a pair of protective release tabs 207 are preferably removably disposed on lower surface 202b and/or adhesive 203. In yet other embodiments, adhesive 203; protective release tabs 207 are omitted.

Pad 204 and raised edges 205 can be an absorbent dressing or gauze and are typically a nonwoven material made from rayon fibers or polyester fibers or a blend of such fibers. It will be apparent to those skilled in the art that other fibers, e.g., cotton fibers or polyolefin fibers may be used in constructing pad 204 and raised edges 205. The pad 204 and/or raised edges 205 can also be made of non-absorbent and/or rigid materials. It should be noted that the pad 204 and raised edges 205 can be made of the same or different materials. The height and dimensions of the raised edges 205 are chosen so that the pad 204 in the hollowed-out area does not touch the user's wound when the raised adhesive bandage 200 is applied. The preferred height of the raised edges 205 depends in part on the compressibility of the material used for it and pad 204. For example, if a highly compressible material like cotton is used, then the height of the raised edges 205 should be higher. The preferred height of the raised edges 205 also depends on the size of the hollowed-out area 206. For example, if the length and width of the hollowed-out area 206 are large, then the height of the raised edges 205 should be higher to prevent the pad 204 in the hollowed-out area 206 from sagging onto the wound. As a general matter, the height "h" of the raised edge should be greater than 1 mm and less than 50 mm to avoid pad 204 from contacting the wound. The raised edges 205 and corresponding formed hollowed-out area 206 can be any shape including, but not limited to, polygonal, quadrilateral, rectangular, square, circular, oblong, triangular, etc. The raised edges 205 separates pad 204 from the user's wound while still protecting it from harmful dirt and debris. Another advantage of this improved configuration is being able to apply less antibiotic ointment to the wound because the offset pad 204 will not soak it up.

Protective release tabs 207 may be made from any material known in the art. These materials include paper having a silicone release material coated thereon and/or may be made of a low surface energy plastic film such as polyethylene or polystyrene which, if desired, may have a silicone release material or the like applied thereto. The release coated surface of protective release tabs 207 will contact adhesive 203 and the release coating on protective release tabs 207 will be such that adhesive 203 will remain on lower surface 202b rather than on protective release tabs 207 when those tabs are removed to expose adhesive 203 prior to application of raised adhesive bandage 200 to the skin. Adhesive 203 is made from any skin-compatible material known in the art, i.e., adhesive free of latex, and/or substantially free of latex.

Raised adhesive bandage 200 and/or strip 202 may be provided in any shape and/or configuration as is known in the art including, but not limited to, polygonal, quadrilateral, rectangular, square, circular, oblong, triangular, etc. The shape of raised adhesive bandage 200 may dictate the number of protective release tabs 207, and/or location of pad 204 on lower surface 202b. For example, if strip 202 is rectangular, pad 204 is preferably in the middle, or substantially middle, of strip 202. If strip 202 is circular, for example, raised adhesive bandage 200 may have a single protective release tab 207.

II. Sectional Raised Adhesive Bandage

Figure 3A:
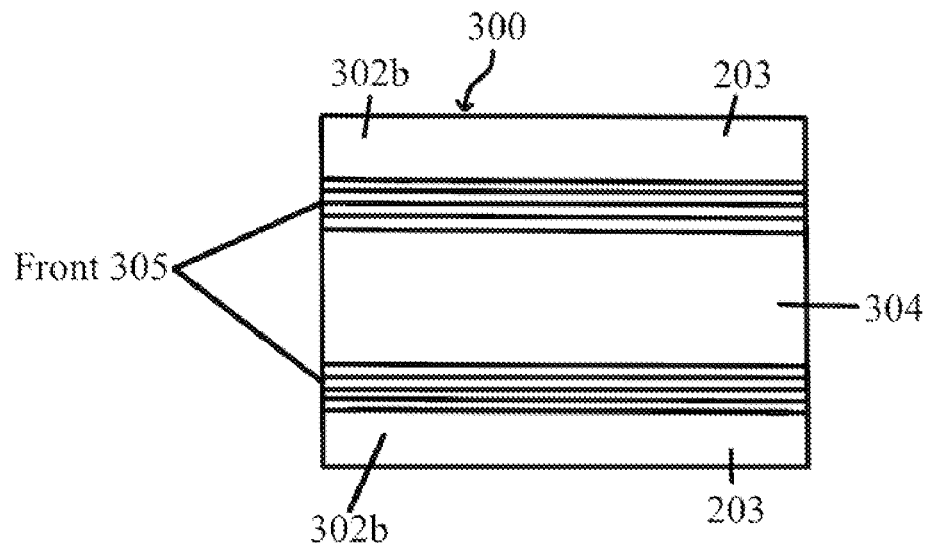
FIG. 3A is a bottom plan view (facing the skin and wound) of a preferred embodiment of the sectional raised adhesive bandage of the present invention where the sectional raised edges are positioned such that the channeled-out area separates the sectional pad from the wound.
Figure 3B:
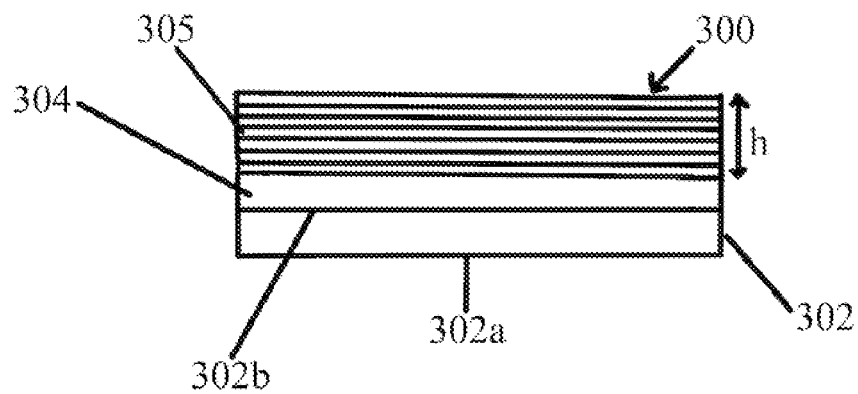
FIG. 3B is a side view of a preferred embodiment of the sectional raised adhesive bandage of the present invention.
Figure 3C:
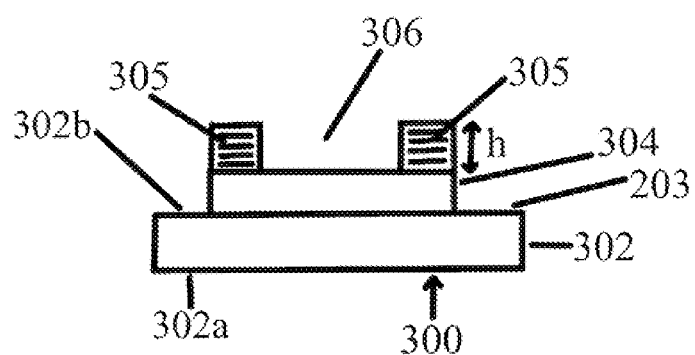
FIG. 3C is the front side view of a preferred embodiment of the sectional raised adhesive bandage of the present invention.

FIGS. 3A-3C show an embodiment of a sectional raised adhesive bandage 300 of the present invention. One or more sectional raised adhesive bandages 300 can be applied over (but not touching) long and/or curved wounds that cannot be effectively covered by a single raised adhesive bandage 200. Sectional raised adhesive bandage 300 preferably includes a sectional strip 302 having a sectional upper surface 302a that faces away from the skin and a sectional lower surface 302b that faces the skin, an adhesive 203, a sectional pad 304, at least two sectional raised edges 305 that create a channeled-out area 306, and a pair of protective release tabs 207. Adhesive 203 is at least partially disposed on sectional lower surface 302b and contacts a user's skin. Sectional pad 304 is disposed on sectional lower surface 302b and/or adhesive 203. Sectional raised edges 305 are disposed on the sectional pad 304 and/or adhesive 203 creating a channeled-out area 306 such that sectional pad 304 does not touch the wound. Sectional raised edges 305 and channeled-out area 306 can be straight or curved depending on the shape of the wound. Sectional raised edges 305 can be one continuous shape or comprised of multiple separate shapes. Protective release tabs 207 are preferably removably disposed on sectional lower surface 302b and/or adhesive 203. The sectional raised edges 305 can, but do not have to, extend to the outer edges of the sectional pad 304.

III. End Sectional Raised Adhesive Bandage

Figure 4A:
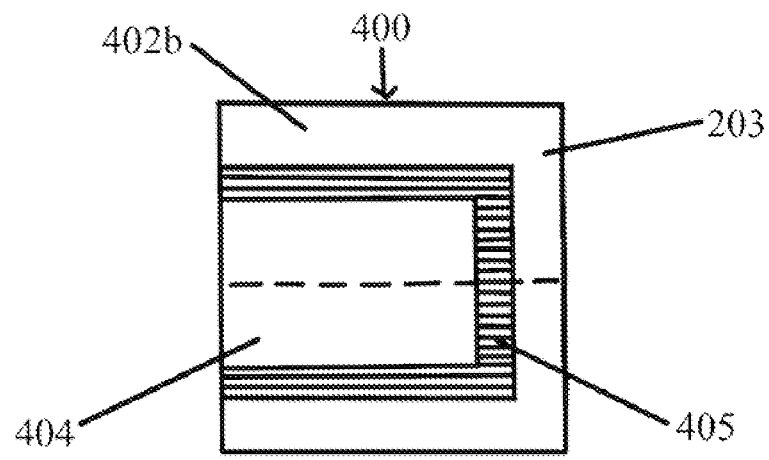
FIG. 4A is a bottom plan view (facing the skin and wound) of a preferred embodiment of the end sectional raised adhesive bandage of the present invention where the end sectional raised edges are positioned such that the partially channeled-out area separates the end sectional pad from the wound.
Figure 4B:
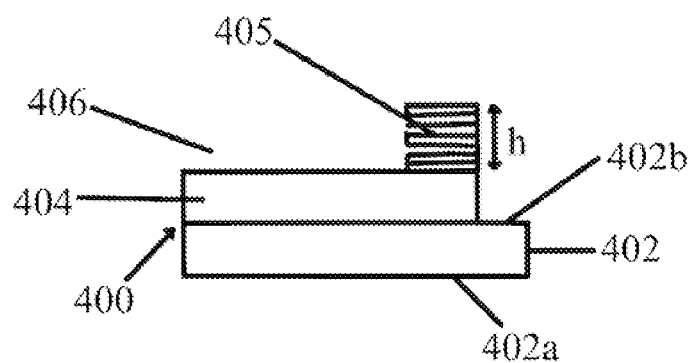
FIG. 4B is a side cut-away slice of a preferred embodiment of the end sectional raised adhesive bandage of the present invention viewed along the center dashed line of FIG. 4A.

FIGS. 4A-4B show an embodiment of an end sectional raised adhesive bandage 400 of the present invention. This embodiment is used at the ends to close off the runs of one or more sectional raised adhesive bandages 300.

End sectional raised adhesive bandage 400 preferably includes an end sectional strip 402 having a sectional upper surface 402a that faces away from the skin and an end sectional lower surface 402b that faces the skin, an adhesive 203, an end sectional pad 404, end sectional raised edges 405 that create a partially channeled-out area 406, and protective release tab(s) 207. Adhesive 203 is at least partially disposed on end sectional lower surface 402b and contacts a user's skin. End sectional pad 404 is disposed on end sectional lower surface 402b and/or adhesive 203. In one preferred embodiment, end sectional raised edges 405 are disposed on three sides of end sectional pad 404 and/or adhesive 203 creating a partially channeled-out area 406. It should be recognized that end sectional raised edges 405 can be any shape and have any number of sides as the purpose is to seal off the end of sectional raised adhesive bandage 300.

IV. System of a Plurality of Contactless Adhesive Bandages

Figure 5:
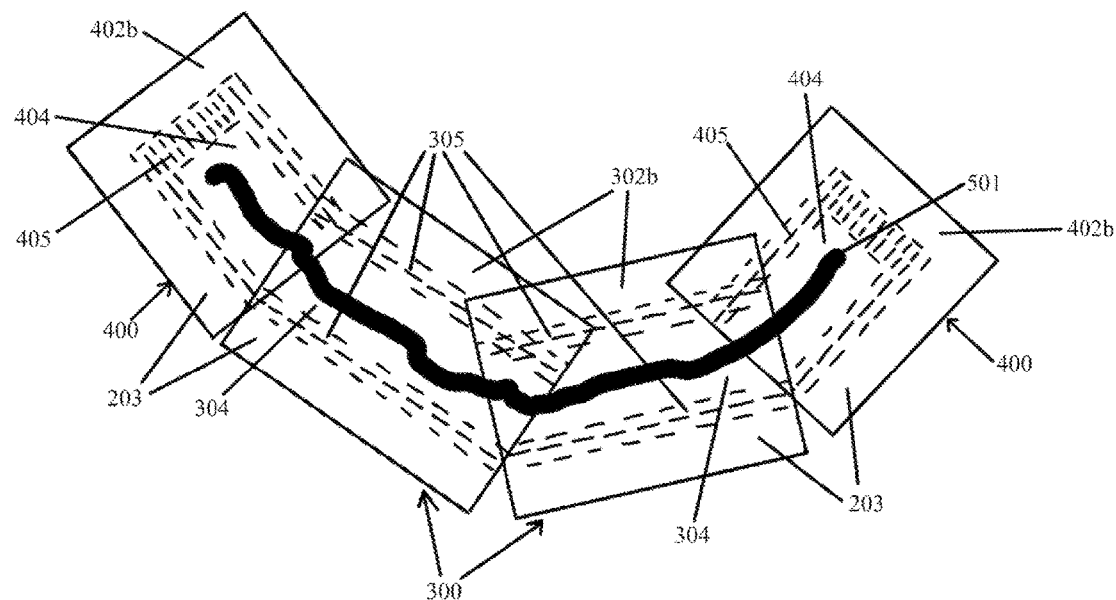
FIG. 5 is a bottom plan view (facing the skin and wound) of a preferred embodiment of a system of contactless adhesive bandages comprising two sectional raised adhesive bandages sealed off by two end sectional raised adhesive bandages that overlap to follow the contours of, but not touch, a long curving wound.
Figure 6:
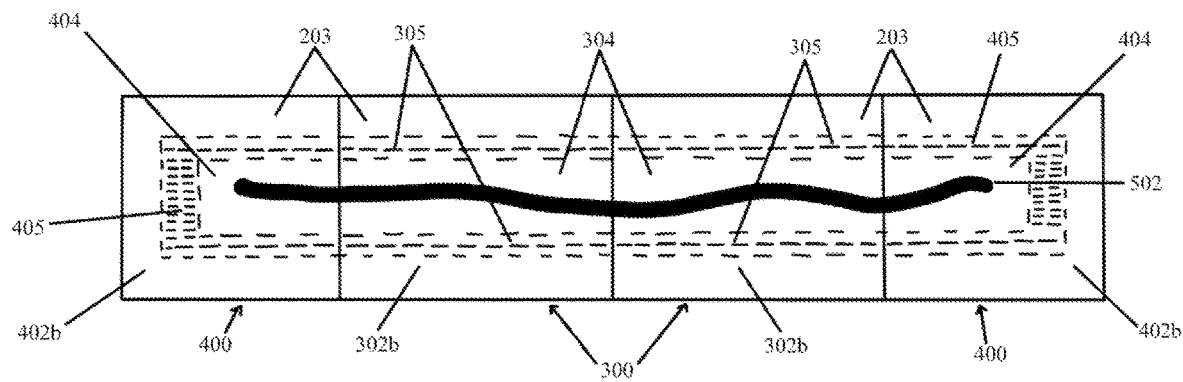
FIG. 6 is a bottom plan view (facing the skin and wound) of a preferred embodiment of a system of contactless adhesive bandages comprising two sectional raised adhesive bandages sealed off two end sectional raised adhesive bandages that are configured to cover, but not touch, a long wound.

FIGS. 5-6 show bottom plan views of a system of a plurality of contactless adhesive bandages applied contiguously. The system is comprised of one or more sectional raised adhesive bandages 300 sealed off on both sides by an end sectional raised adhesive bandage 400. It should be recognized that any number of sectional raised adhesive bandages 300 and/or end sectional raised adhesive bandages 400 can be used to create a completely configurable and extendible system of a plurality of contactless adhesive bandages to cover, but not contact, wounds 501 and 502 of any shape or size. FIG. 5 shows how the contours of a curving wound 501 can be covered with overlapping contactless adhesive bandages. FIG. 6 shows how a long wound 502 can be covered with extendible contactless adhesive bandages that do not overlap. It is evident that the system of a plurality of contactless adhesive bandages can be overlapping, non-overlapping, or a combination thereof.

V. Common Characteristics

The description, material, and dimensional properties of pad 204 applies to sectional pad 304 and end sectional pad 404. Likewise, the description, material, and dimensional properties of raised edges 205 applies to sectional raised edges 305 and end sectional raised edges 405.

Strip 202, sectional strip 302, and end sectional strip 402 may be comprised of any material, such as fabric, plastic, plaster, and the like. These and/or their corresponding upper surfaces (i.e., 202a, 302a, 402a) may be colored to match the skin tones of a person or are see-through. Furthermore, the strips (i.e. 202, 302, 402) can be waterproof preventing their pads (i.e., 204, 304, 404) and raised edges (i.e., 205, 305, 405) from getting wet thereby reducing the need to change the raised adhesive bandages (i.e., 200, 300, 400) after being exposed to external elements (e.g., water).

In other embodiments, pad 204, sectional pad 304, end sectional pad 404 are not used. Raised edges 205, sectional raised edges 305, and end sectional raised edges 405 are disposed on lower surface 202b, sectional lower surface 302b, end sectional lower surface 402b, respectively, and/or adhesive 203. Preferably but not required, a see-through material is used for strip 202, sectional strip 302, and end sectional strip 402 so that the user can easily see to align the hollowed-out area 206, channeled-out area 306, and partially channeled-out area 406, respectively, over, but not touching, the wound. The see-through material will also allow the user monitor the healing of the wound without removing the raised adhesive bandage 200, sectional raised adhesive bandage 300, and end sectional raised adhesive bandage 400.

Although the preferred embodiments describe pad 204, sectional pad 304, end sectional pad 404, raised edges 205, sectional raised edges 305, and end sectional raised edges 405 as not touching the wound, it is understood that in certain embodiments it may be necessary and/or beneficial for these to at least partially touch the wound.

The raised adhesive bandages 200, sectional raised adhesive bandages 300, and end sectional raised adhesive bandages 400 of the present inventions may be individually packaged between two sheets of paper which are sealed cohesively about the edges.

It is to be understood that the present invention can be used with any adhesive bandage now known or later contemplated.

VI. Wound Tape/Gauze/Cover-Up

In another embodiment, the invention is directed to using wound tape in place of strip 202, sectional strip 302, end sectional strip 402; and/or gauze material for pad 204, sectional pad 304, end sectional pad 404; and raised edges 205, sectional raised edges 305, end sectional raised edges 405. Wound tape holds dressings or bandages around the wound site. Gauze is a surgical dressing that may be secured by medical tape and/or self-adherent wrap. The wound tape or gauze may have an upper surface and a lower surface. Preferably, the upper surface faces away from the user's skin, and the lower surface faces the user's skin.

We claim:

1. A system of plurality of contactless adhesive bandages that are contiguously applied so as to be customizable configured to extend and cover the contours of, but not touch, a wound comprising:

one or more sectional raised adhesive bandages contiguously applied to cover, but not contact, the wound each comprising:
a sectional strip layer comprising a sectional upper surface that faces away from the skin and a sectional lower surface that faces the skin; a first adhesive is at least partially disposed on the sectional lower surface; a lower sectional pad layer is disposed on the first adhesive and/or sectional lower surface; wherein a material of the lower sectional pad layer consists of an absorbent material; sectional raised edges comprising two sides disposed on the lower sectional pad layer and/or first adhesive creating a channeled-out area; and the sectional raised edges are dimensioned such that the sectional raised edges and the lower sectional pad layer are not in contact with the wound when the sectional raised adhesive bandage is applied; wherein a material of the sectional raised edges consists of an absorbent material; a first end sectional raised adhesive bandage that seals off a first end of the one or more sectional raised adhesive bandages; a second end sectional raised adhesive bandage that seals off a second end of the one or more sectional raised adhesive bandages; wherein the first and second end sectional raised adhesive bandages are configured to cover, but not contact, the wound each comprising:
an end sectional strip layer comprising an end sectional upper surface that faces away from the skin and an end sectional lower surface that faces the skin; a second adhesive is at least partially disposed on the end sectional lower surface; a lower end sectional pad layer is disposed on the second adhesive and/or end sectional lower surface; wherein a material of the lower end sectional pad layer consists of an absorbent material; end sectional raised edges comprising at least two sides on the lower end sectional pad layer and/or second adhesive creating a partially channeled-out area; and the end sectional raised edges are dimensioned such that the end sectional raised edges and the lower end sectional pad layer are not in contact with the wound when the end sectional raised adhesive bandage is applied; wherein a material of the end sectional raised edges consists of an absorbent material; wherein the sectional raised edges and end sectional raised edges are aligned to form the channeled-out area that is continuous and configured to cover and protect the wound.

2. The system of plurality of contactless adhesive bandages of claim 1, wherein the lower sectional pad layer and sectional raised edges include rayon fibers.

3. The system of plurality of contactless adhesive bandages of claim 1, wherein the lower sectional pad layer and sectional raised edges include polyester fibers.

4. The system of plurality of contactless adhesive bandages of claim 1, wherein the lower end sectional pad layer and end sectional raised edges include rayon fibers.

5. The system of plurality of contactless adhesive bandages of claim 1, wherein the lower end sectional pad layer and end sectional raised edges include polyester fibers.

6. The system of plurality of contactless adhesive bandages of claim 1, that are contiguously applied in an overlapping fashion.

7. The system of plurality of contactless adhesive bandages of claim 1, that are contiguously applied in a non-overlapping fashion.

8. The system of plurality of contactless adhesive bandages of claim 1, that are contiguously applied in an overlapping and non-overlapping fashion.

9. The system of plurality of contactless adhesive bandages of claim 1, wherein each of the sectional strip layers of the at least one sectional raised adhesive bandage comprise two sides configured to contact a user's skin adjacent to the wound; wherein each of the end sectional strip layers of the first and second end sectional raised adhesive bandages comprise at least two sides configured to contact the user's skin adjacent to the wound.

* * * * *